United States Patent [19]

Obayashi

[11] Plant 4,035

[45] Apr. 5, 1977

[54] DRACAENA PLANT

[75] Inventor: Hideo Obayashi, Totohashi, Japan

[73] Assignee: Cerro Gordo, Inc., Dorado, P.R.

[21] Appl. No.: 686,662

[22] Filed: May 14, 1976

[51] Int. Cl.[2] ..... A01H 5/12
[52] U.S. Cl. ..... Plt./88
[58] Field of Search ..... Plt./88

*Primary Examiner*—Robert E. Bagwill
*Attorney, Agent, or Firm*—J. Gibson Semmes

EXEMPLARY CLAIM

1. The new and distinct variety of dracaena plant substantially as herein shown and described, characterized particularly by medium long, narrow, sword-shaped, dense spreading leaves, the leaves being compactly grouped and erect, the texture thereof being hard and the distinctive color pattern of its leaves with a marginal red-pink strip widening from base to apex, a less prominent mid-rib pink stripe merging with the marginal stripe at the apex, two green stripes on either side of the mid-rib stripe, widening from base to apex, coloration of all stripes on both sides being substantially the same.

1 Drawing Figure

1

A new distinct variety of ornamental plant of the genus Dracaena originated as a mutation of an unpatented variety of *Dracaena marginata.*

The mutation was discovered in the nursery located at 61-2 Montomachi, Minamiohshimizu-cho, Toyohashi City, Aichi Prefecture, Japan.

It has been asexually reproduced at the same location by means of cuttings and its distinguishing features appeared to be permanent.

The accompanying illustration depicts a color photograph of a potted plant of the new variety in approximately its true colors, the plant shown being approximately 40 weeks old at the time of photographing. The specimen was at that time approximately 16 inches tall from the ground to the tip of the central leaf.

In the following detailed description of my new variety, the color method chosen for identification has been taken of the Inter-Society Color Council-National Bureau of Standards, Supplement to Circular 553, the ISCC Method of designating Color and a Dictionary of color names.

The new variety is a herbaceous plant and has medium long, narrow, sword shaped, dense spreading leaves 5 to 14 inches in length. The width of the leaves varies from ¼″ to ⅞″. As in the mother plant *Dracaena marginata*, the leaves are compactly grouped and pendant. The texture of the leaves is the same as in the mother plant.

The habit of growth is somewhat slower than the parent, growing about 12 inches the first year if allowed to grow without cutting. Because of the pleasing color pattern, this new variety makes an excellent house plant. It propagates true from cuttings, rooting easily at each node which is placed below the earth surface.

Among outstanding features are included the novel striping of the leaves, represented by a marginal red-pink stripe (No. 12 Strong Red) on both margins, 1/16

2 inch in width at the base and at the apex, widening gradually to ⅛ inch between the base and the apex. There is a less prominent pink mid-rib stripe extending from the base of the leaves to the apex, (Color No. 2 Strong Pink), there being also a tendency for this mid-rib stripe to merge towards the apex with the marginal red-pink stripe. There are two green stripes (No. 111 Dark Green 01) on each side of the aforesaid mid-rib stripe, and between the marginal stripes. These green stripes are 1/16 inch in width at the base and widen gradually to ⅛ inch between the base and the apex. Coloration of all stripes aforesaid on both sides of the leaves appears to be the same.

COMPARISONS

The principal differences between the varieties lie in the color pattern and shape of their leaves as follows:

1. The color pattern of the leaves of the new variety *Dracaena colorama* consist of: a wider and more distinctive marginal red-pink stripe.
2. Where the green is predominant in the *Dracaena marginata*, there is a greater proportion of red and pink in this new variety.
3. The leaves of the mutant hereof are somewhat narrower and have a more pendant tendency than the parent *Dracaena marginata.*

Having thus disclosed my discovery, I claim:

1. The new distinct variety of Dracaena plant substantially as herein shown and described, characterized particularly by medium long, narrow, sword-shaped, dense spreading leaves, the leaves being compactly grouped and erect, the texture thereof being hard and the distinctive color pattern of its leaves with a marginal red-pink strip widening from base to apex, a less prominent mid-rib pink stripe merging with the marginal stripe at the apex, two green stripes on either side of the mid-rib stripe, widening from base to apex, coloration of all stripes on both sides being substantially the same.

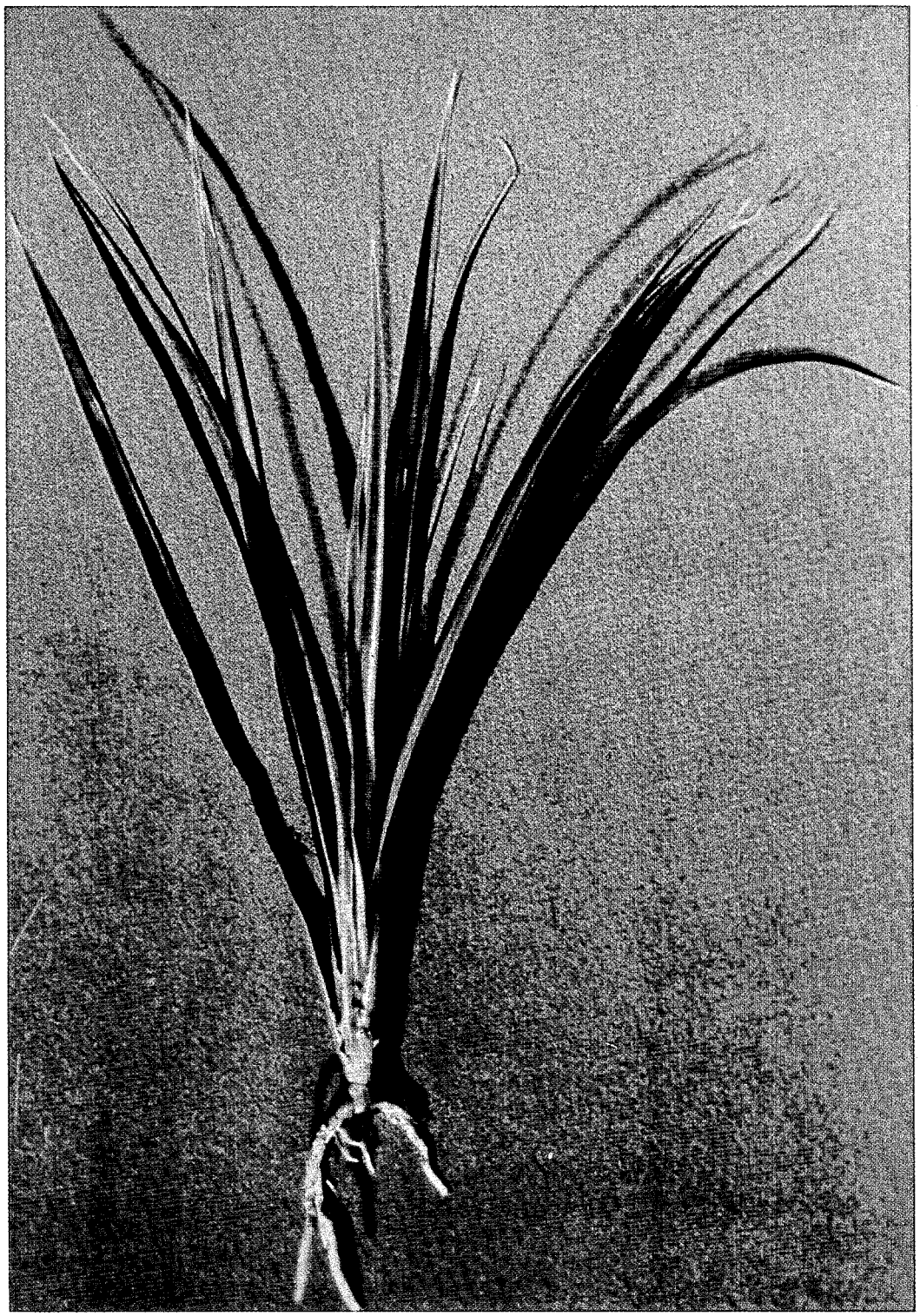

* * * * *